United States Patent [19]

Hass, Jr. et al.

[11] Patent Number: 4,984,462
[45] Date of Patent: Jan. 15, 1991

[54] DETACHABLE LIQUID LEVEL MONITORING APPARATUS AND METHOD

[75] Inventors: Robert D. Hass, Jr., Corvalis, Oreg.; Brian G. Hodder, Briarwood; Christopher P. Yakymyshyn, Ithaca, both of N.Y.

[73] Assignee: Meditor Corporation, Briarwood, N.Y.

[21] Appl. No.: 358,896

[22] Filed: May 30, 1989

[51] Int. Cl.⁵ .................... G01F 23/02; G01N 21/41
[52] U.S. Cl. .................................. 73/293; 250/577; 340/619; 604/404
[58] Field of Search ................. 73/293; 604/404; 340/619; 222/66; 250/577

[56] References Cited

U.S. PATENT DOCUMENTS

| | | | |
|---|---|---|---|
| 352,647 | 11/1886 | Ghegan | 340/619 |
| 3,138,023 | 6/1964 | Washburn | 73/295 X |
| 3,851,181 | 11/1974 | Heule | 250/577 |
| 4,042,796 | 8/1977 | Zink | 200/61.45 |
| 4,135,400 | 1/1979 | Maxwell et al. | 374/183 X |
| 4,193,004 | 3/1980 | Lobdell et al. | 250/577 |
| 4,440,022 | 4/1984 | Mason | 340/619 X |
| 4,733,095 | 3/1988 | Kurahashi et al. | 250/577 |
| 4,749,276 | 6/1988 | Bragg et al. | 356/440 X |
| 4,820,925 | 4/1989 | Balmer et al. | 250/379 |
| 4,840,137 | 6/1989 | Beauvais et al. | 73/293 X |

Primary Examiner—Daniel M. Yasich
Attorney, Agent, or Firm—Flehr, Hohbach, Test, Albritton & Herbert

[57] ABSTRACT

Liquid level monitoring apparatus for monitoring the level of a liquid in a container having a wall with an exterior surface and an interior surface and formed of a material which is substantially transparent to optical energy and which has an index of refraction different from that of the liquid. The apparatus comprises an optical sensor holder and adhesive means adapted to secure the sensor holder to the exterior surface of the container at a predetermined level. A sensor head is provided. An attachment mechanism is carried by the sensor head and the sensor holder for detachably mounting the sensor head on the sensor holder. A self-contained power supply is provided which is coupled to the sensor head.

19 Claims, 4 Drawing Sheets

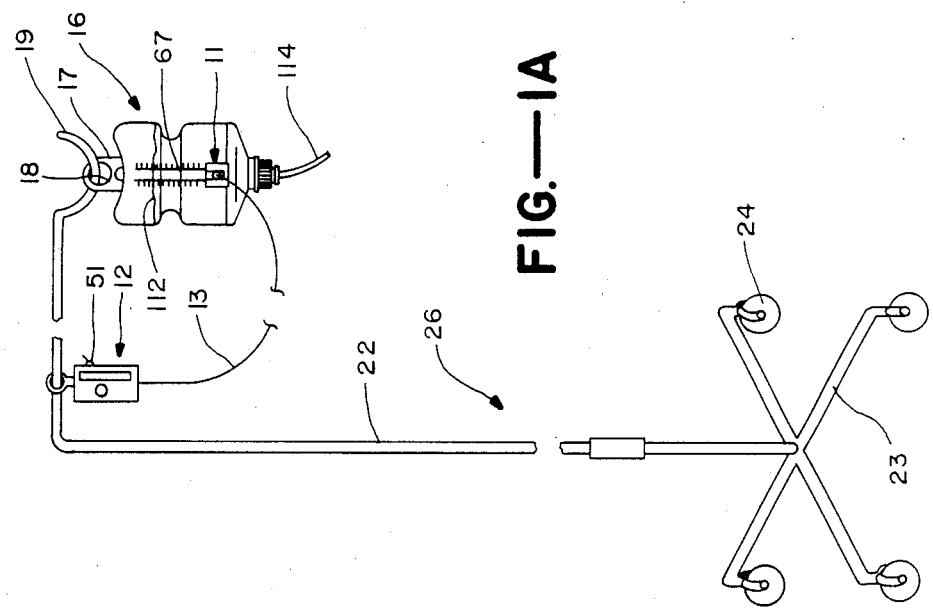
FIG.—1A
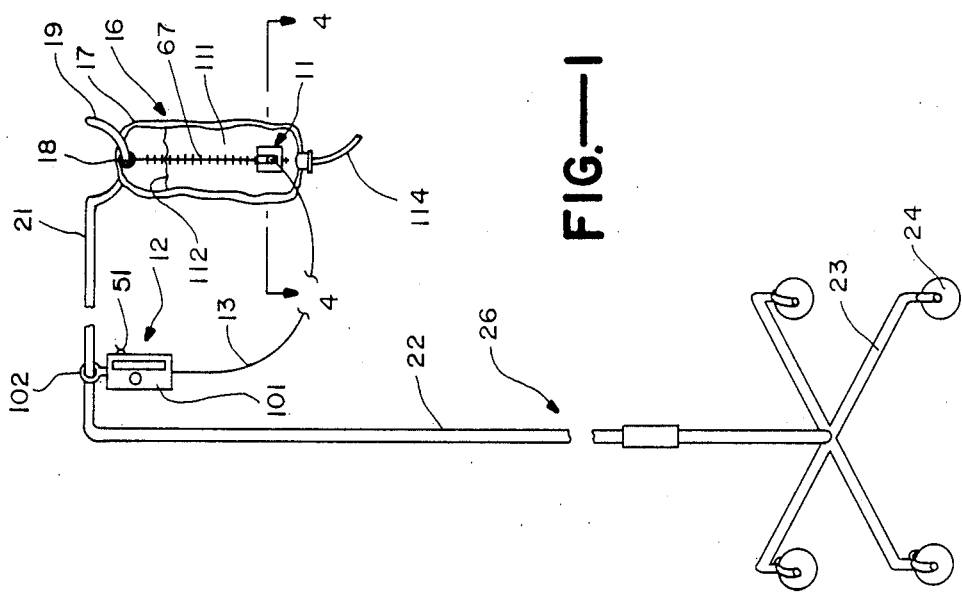
FIG.—1

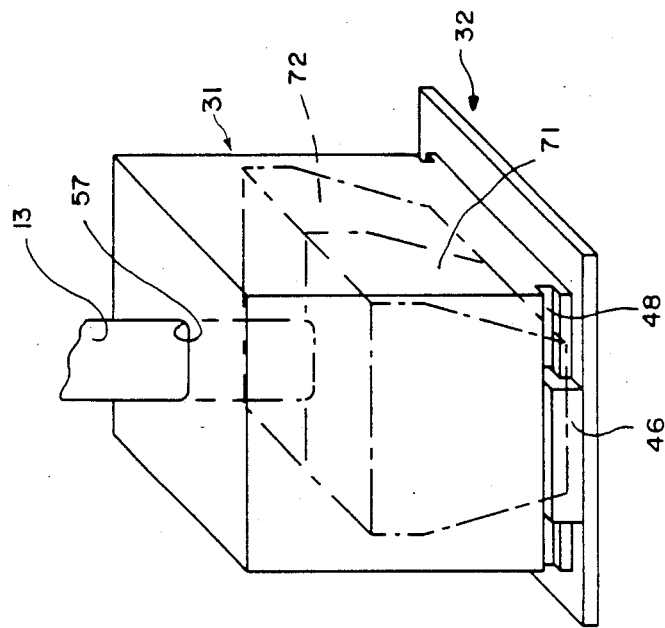
FIG.—3
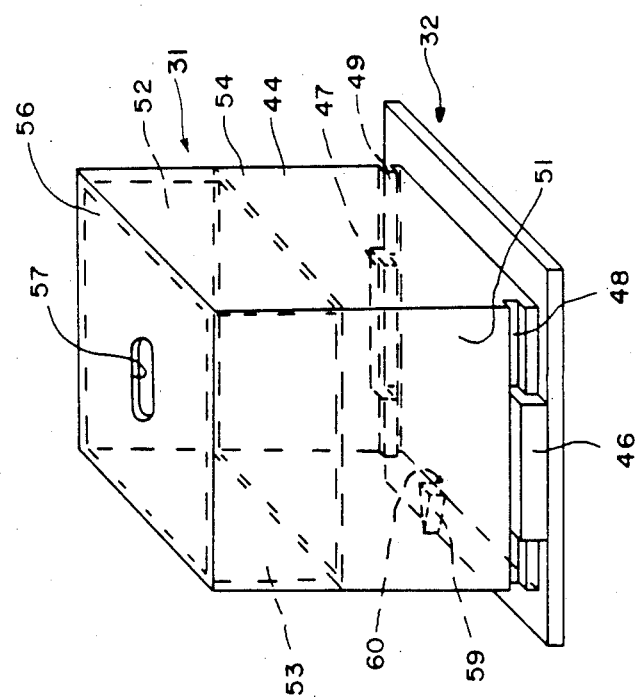
FIG.—2

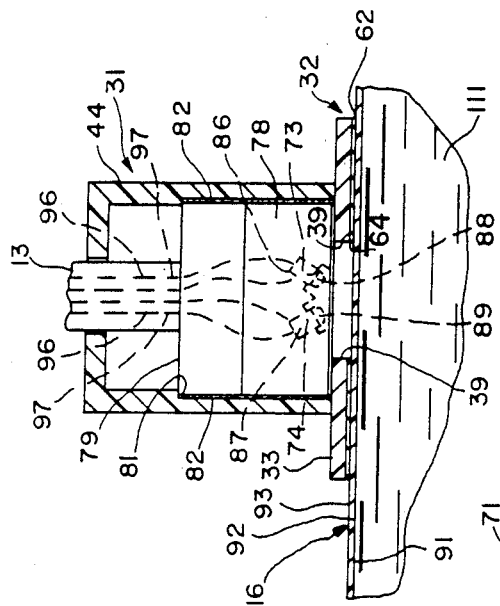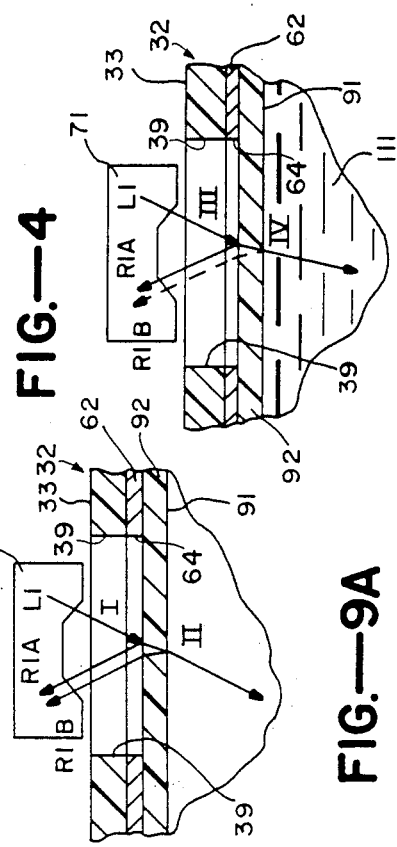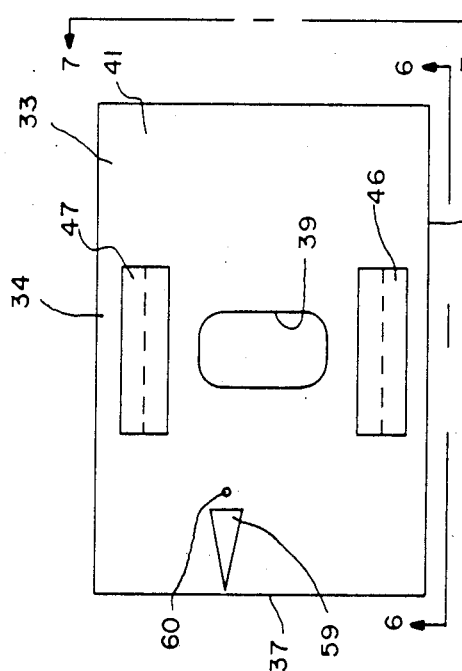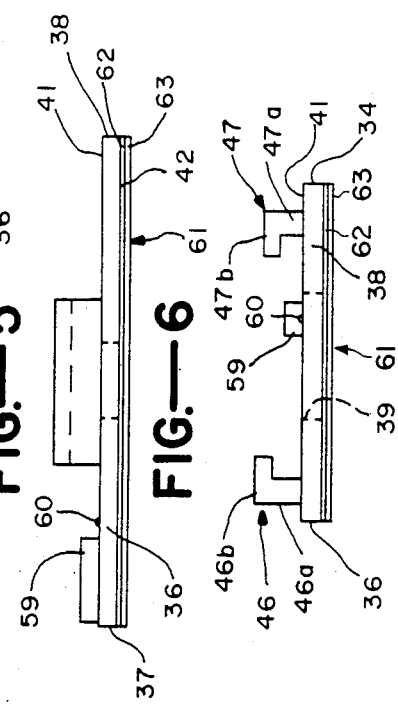

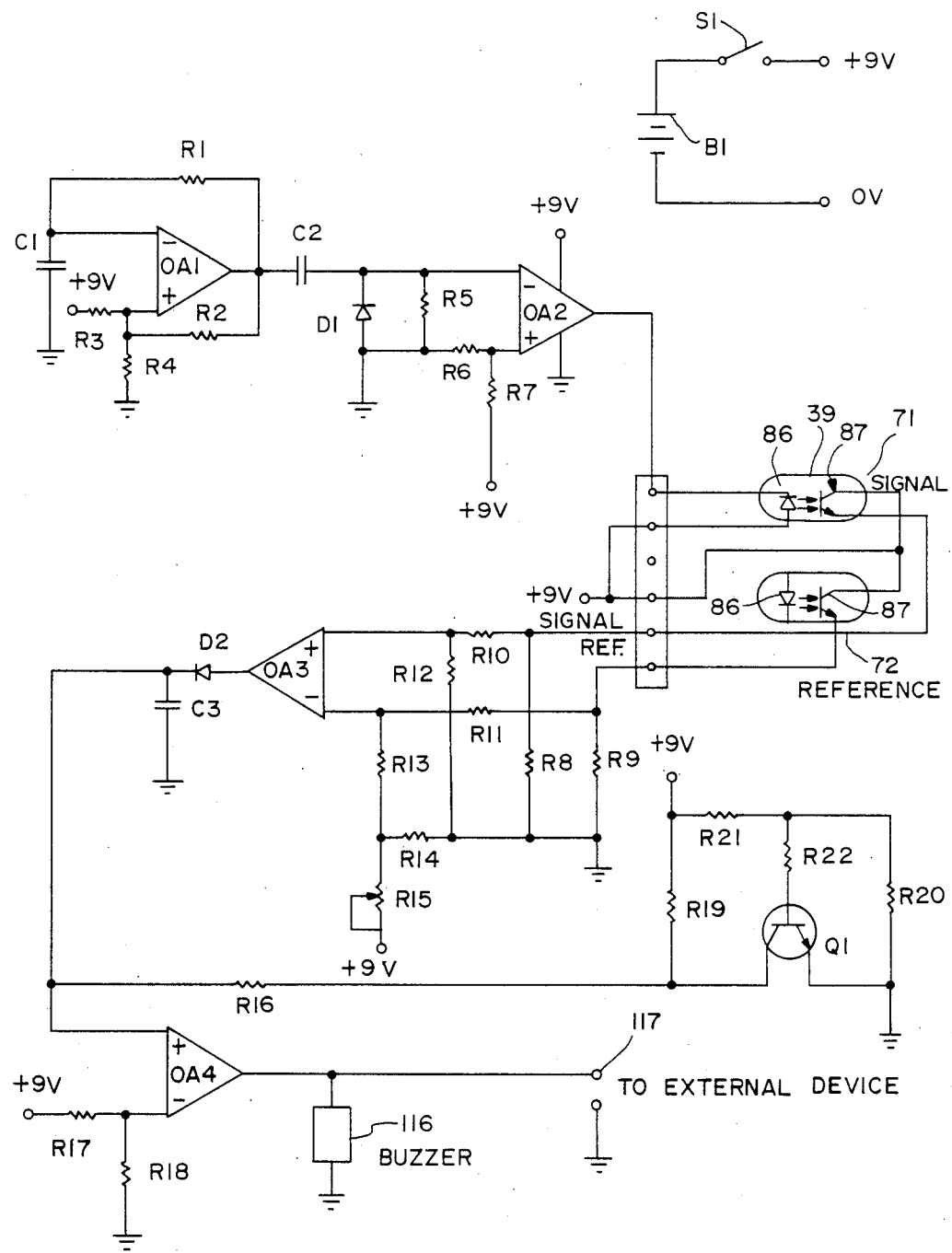
FIG.—8

DETACHABLE LIQUID LEVEL MONITORING APPARATUS AND METHOD

This invention relates to a detachable liquid level monitoring apparatus and method.

Liquid level apparatus has heretofore been provided particularly for use with intravenous bags or bottles to indicate when the bag becomes nearly empty and requires replacement. A typical device is disclosed in U.S. Pat. No. 3,588,859 which discloses a level detector which uses a capacitance bridge. Such devices still have a number of disadvantages. They are not self-contained. They are not readily detachable from the bag or bottle. There is therefore a need for a new and improved liquid level monitoring apparatus and method of using the same.

In general, it is an object of the present invention to provide a liquid level monitoring apparatus which is particularly suitable for rigid bottles and flexible bags.

Another object of the invention is to provide an apparatus and method of the above character in which an opto-electronic sensor is utilized.

Another object of the invention is to provide an apparatus and method of the above character in which an adhesive backed mounting pad is adapted to be applied to the bag or bottle.

Another object of the invention is to provide an apparatus and method of the above character in which the sensor is removably attached to the mounting pad.

Another object of the invention is to provide an apparatus and method of the above character in which the pad is discarded with the container.

Another object of the invention is to provide an apparatus and method of the above character which will operate with colored liquids.

Another object of the invention is to provide an apparatus and method of the above character which has a self-contained power supply.

Another object of the invention is to provide an apparatus and method of the above character in which circuitry is provided to maximize battery life.

Another object of the invention is to provide an apparatus and method of the above character which is self-contained and can be moved with the patient.

Another object of the invention is to provide an apparatus and method of the above character which does not require the use of power cables.

Another object of the invention is to provide an apparatus and method of the above character in which periodic testing of the fluid level occurs.

Another object of the invention is to provide an apparatus and method of the above character which relies upon reflections which occur at the interface between the wall of the container and the liquid utilized.

Another object of the invention is to provide an apparatus and method of the above character which relies upon reflections that change in magnitude.

Another object of the invention is to provide an apparatus and method of the above character in which reflections are calculated using a Fresnel equation.

Another object of the invention is to provide an apparatus and method of the above character in which the effect of stray light is minimized.

Another object of the invention is to provide an apparatus and method of the above character in which a focused source and detector are utilized to make the sensor less immune to stray light.

Another object of the invention is to provide an apparatus and method of the above character in which an additional reference sensor is utilized to provide immunity from stray light.

Another object of the invention is to provide an apparatus and method of the above character in which pulse operation of the sensor source is utilized to make the apparatus more immune to stray light.

Additional objects and features of the invention will appear from the following description in which the preferred embodiments are set forth in detail in conjunction with the accompanying drawings.

FIG. 1 is an isometric view of a detachable liquid level sensing apparatus mounted on an IV bag supported on an IV stand.

FIG. 1A is a view similar to FIG. 1 but showing the liquid level monitoring apparatus of the present invention being mounted on an IV bottle supported on an IV stand.

FIG. 2 is an isometric view of the sensor head housing utilized in the apparatus shown in FIGS. 1 and 1A.

FIG. 3 is an isometric view of the electronic sensor heads mounted in the housing in the apparatus shown in FIGS. 1 and 1A.

FIG. 4 is a cross sectional view taken along the line 5—5 of FIG. 1 showing the sensor head secured to the IV bag.

FIG. 5 is a front elevational view of the sensor head attachment pad.

FIG. 6 is a bottom view of the pad shown in FIG. 5 looking along the line 6—6 of FIG. 5.

FIG. 7 is a side elevational view of the pad shown in FIG. 5 looking along the line 7—7 of FIG. 5.

FIG. 8 is a circuit diagram of the electronic circuitry utilized in the apparatus shown in FIGS. 1 and 1A.

FIGS. 9A and 9B are schematic illustrations showing the method and manner of operation of the apparatus for sensing the liquid level in a bag or a bottle.

In general, the liquid level monitoring apparatus is used for monitoring the level of a liquid in a container formed of a material which is substantially transparent to infrared energy and which has an exterior and an interior surface. The apparatus comprises a pad. Adhesive means is provided for securing the pad to the exterior surface of the container. An opto-electronic sensor head is provided. Cooperative means is provided on the head and the pad for detachably mounting said head on said pad. A self-contained power supply is provided which is coupled to the sensor head.

The method for detecting the level of a liquid in a container having a wall formed of a material which is substantially transparent and having an exterior surface and an interior surface and an index of refraction different from the index of refraction of the liquid in the container is accomplished by directing optical energy through the wall of the container so that energy is reflected from the exterior and interior walls of the container. The method further comprises detecting the reflection of energy from one of the exterior and interior surfaces of the wall of the container and detecting when a change occurs in the reflections from the one wall of the container to ascertain when the liquid level falls below a predetermined level in the container.

More in particular the liquid level monitoring apparatus comprising the present invention consists of a sensing unit 11 and a monitor unit 12 which are interconnected by a cable 13. This liquid level monitoring apparatus 11 is utilized for monitoring the liquid level in a container 16. The container 16 can be of any suitable type. However, in connection with the present invention it is desired that the container be formed of a material which is substantially transparent to optical energy, as for example, infrared energy. The container 16 can be formed of a flexible bag as shown in FIG. 1 which is typically used for dispensing medical solutions such as IV solutions to a patient. It also can be in the form of a rigid container such as shown in FIG. 1A also formed of a suitable material such as plastic. Also containers such as glass bottles which are circular in cross section can be utilized. Each of the containers 16 is provided with a hanger portion 17 which is provided with a hole 18 to permit the hanger portion 17 to be mounted on and supported by the arcuate extremity 19 of a generally horizontally extending support member or arm 21 which is formed as a part of a vertical support pole 22. The support can be of a conventional telescoping type mounted upon a cross frame 23 provided with casters 24, all of which form a part of an IV support stand 26. The support stand 26 is of a conventional type and can be readily moved with the patient as hereinafter described.

The sensing unit 11 consists of the sensor head 31 which is removably attached to a sensor holder 32 (see FIGS. 2 and 3). The sensor holder 32 is shown in detail in FIGS. 5, 6 and 7 and consists of a plate-like member 33 formed of a suitable material such as a rigid plastic which is generally rectangular in configuration having spaced apart top and bottom edges 34 and 36 and spaced apart parallel side edges 37 and 38 that extend in directions perpendicular to the edges 34 and 36. An elongate generally rectangular opening 39 is provided in the plate-like member 38 and extends through the parallel planar surfaces 41 and 42 of the plate-like member 33. The major axis of the opening 39 extends in a direction which is parallel to the side edges 37 and 38 and its minor axis extends in a direction which is parallel to the top and bottom edges 34 and 36. The inside corners of the opening 39 are rounded as shown.

The sensor head 31 is provided with a case or housing 44 which can be formed of a suitable material such as plastic. Cooperative mating means is provided on the case or housing 44 of the sensor head 31 and the plate-like member 33 of the sensor holder to permit attachment of the sensor head 31 to the sensor holder 32 or detachment of the sensor head from the sensor holder 32. Such cooperative mating means can take a number of forms. For example, as shown in the drawing, such cooperative mating means can consist of L-shaped members 46 and 47 which are formed integral with the plate-like member 33. Alternatively if desired, the retaining members 46 and 47 can be formed of separate parts and then secured to the plate-like member 33 by suitable means such as an adhesive or screws. The retaining members 46 and 47 are L-shaped in cross section. Thus the retaining member 46 is provided with a portion 46a which extends perpendicular to the surface 41 of the plate-like member 33 and a portion 46b which extends in a direction which is generally parallel to the surface 41 and inwardly from the side edge 38. Similarly, the retaining member 47 is provided with an upwardly extending portion 47a and an inwardly extending portion 47b. Spaced apart parallel slots or recesses 48 and 49 are provided in the two spaced parallel walls 51 and 52 of the case or housing 44 on opposite sides of the housing 44 which are adapted to receive the portions 46b and 47b of the retaining members 46 and 47.

The recesses 48 and 49 extend in a direction perpendicular to walls 53 and 54 of the case or housing 44. The case or housing 56 is also provided with a top wall 56 which has an opening 57 therein through which the cable 13 extends.

Suitable means is provided to ensure that the case 44 can be inserted into the slots 48 in only one orientation of the case. In the present embodiment this is accomplished by having one of the slots 48 and 49 be at a higher elevation on the associated wall than the other slot. Similarly one of the L-shaped retaining members 46 and 47 extends at a higher elevation than the other retaining member. Thus the retaining member 46 extends above the surface 41 at a greater distance than the retaining member 47, and the slot or recess 48 extends at an elevational which is higher than that of the slot 49 so that the case can only be inserted into the retaining members in one orientation. The fit between the retaining members 46 and 47 and the slots or recesses 48 and 49 is relatively tight so that the case or housing is frictionally retained within the sensor holder 32.

Suitable means is provided for preventing movement of the sensor head 31 beyond a predetermined location on the plate-like member 33 so that it will be properly positioned with respect to the opening 39 and consists of a stop member 59 formed integral with the plate-like member 33 and extending upwardly from the surface 41. As shown it can be generally rectangular so that it is engaged by the outer side of the wall 53 of the case 44.

A detent lug 60 is positioned near the stop member 59 to retain the sensor head 31 on the plate-like member 33. The detent lug extends upwardly from the surface 41 of the plate-like member and engages the inner side of the case wall 53 when the sensor head is in the proper position on the plate-like member. The detent lug is relatively short and is rounded so that the sensor head snaps into place as the wall 53 passes over the lug. Like the stop member 59, the detent lug 60 is formed as an integral part of the plate-like member.

Adhesive attaching means 61 (see FIGS. 6 and 7) is provided for securing the sensor holder 32 to the container 16. The adhesive attaching means 61 can be in any suitable form. For example, it can be comprised of a pressure sensitive layer 62 of an adhesive which is mounted on the surface 42 of the plate-like member 31. The adhesive layer 62 is covered with a removable flexible protective sheet 63 which can of paper or other suitable material which overlies the layer 62 and protects the same until the sensor holder 32 is ready to be used. When it is desired to utilize the sensor holder 32, the sheet 63 can be peeled away from the pressure sensitive adhesive layer 62 and the holder 32 secured to the container 16 in the desired location. The pressure sensitive adhesive 62 is provided with an aperture 64 (see FIG. 4) which is in registration with the opening 39 in the member 33. The stop member 59 can be used as a guide to facilitate positioning of the sensor holder 32 at the desired elevation on the container 16 relative to level markings 67 (see FIGS. 1 and 1A) provided on the container.

Sensor modules 71 and 72 forming a part of the sensor head 31 are provided within the case or housing 44. The modules 71 and 72 can be formed of a suitable material such as plastic. Each of the modules is provided with a pair of bores 73 and 74 aligned at a suitable angle as, for example, 45° with respect to a front surface 76 provided on the modules 71 and 72. The two modules 71 and 72 are positioned within the case or housing 44 in such a manner that the front surface 76 is generally in alignment with the forward extremity of the housing or case 44 and is immediately adjacent the sensor opening 39. Each of the modules 71 and 72 is provided with inclined sidewalls 77 and 78 which adjoin the front surface 76. Each of the modules 71 and 72 is also provided with a rear wall 79 which is adapted to seat against a shoulder 81 formed within the case 44. The modules 71 and 72 can then be held in the desired position against the shoulder 81 in the case 44 by a suitable means such as an epoxy 82.

Optical level sensing means in the form of a sensor pair is provided in each of the modules 71 and 72 and consists of a source of optical energy as, for example, an infrared source such as a light emitting diode (LED) 86 (FIG. 4) mounted in the bore 73 and a photoelectric detector 87 for detecting the infrared light from the LED source 86 is provided in the other bore 74. Lenses 88 and 89 are provided in the bores 73 and 74 and are positioned so their focal points are at the same point on the inside surface 91 of the wall 92 of the container 16. The outside surface 93 of the wall 92 has the pressure sensitive adhesive layer 62 bonded to the same as shown in FIG. 4. Wires 96 from the cable 13 are connected to the light emitting diode 86 and the detector 87 by connecting the wires 96 to conducting posts 97 carried by the modules 71 and 72 connected to the light emitting diode 86 and the detector 87.

Alternatively, the sensing head can be formed as a unitary structure with the optical sensors being molded into the case rather than being mounted separately as to the present embodiment. This would reduce the cost of the device by reducing the number of parts and eliminating the steps required to mount the sensors, and it would also provide more uniform alignment of the sensors.

The cable 13 extends to the monitor unit 12 which consists of a box-like case 101 formed of a suitable material such as plastic and which has mounted therein a printed circuit board (not shown) which carries the electronic circuitry which is shown in FIG. 8. An on-off switch 106 is mounted in the case 101 for turning the electronic circuitry on and off. The case 101 also contains self-contained power supply means in the form of a 9-volt battery B1 which under the control of switch S1 as shown in FIG. 8 controls the application of the 9 volts to the electronic circuitry.

The light emitting diode 86 and the detector 87 in each of the modules 71, 72 form a sensor pair. The sensor pairs are disposed horizontally with the upper module 71 serving as the signal sensor pair and the lower module 72 serving as the reference sensor pair. Alternatively, the two sensor modules can be positioned side-by-side, rather than being separated vertically. This would position both sensor pairs at the same height and would eliminate the need to install the sensor head on the mounting plate in the same direction every time.

The electronic circuitry as shown in FIG. 8 includes four operational amplifiers OA1, OA2, OA3 and OA4 which are connected to various electronic components shown in FIG. 8 to operate in the manner hereinafter described. It will be noted that operating power is applied to the light emitting diode 86 in the module 72 and that the sensor in this module operates in a passive mode to monitor ambient light.

Operation and use of the liquid level monitoring apparatus may now be briefly described as follows in performing the method of the present invention. Let it be assumed that it is desired to utilize the liquid level monitoring apparatus in a critical care application, as for example, a situation in which it is desired to monitor the liquid level in an IV bag or container 16 having a liquid 111 therein having a liquid level 112 so that an alarm is initiated when the liquid level 112 approaches a level mandating replacement of the bag or container 16. The monitoring unit 12 can be placed on the IV support stand 26 by utilizing the hanger 102 to mount the same on the horizontal member 21 as shown in FIGS. 1 and 1A. A sensor holder 32 can then be secured to the bag in the appropriate location by first removing the protective sheet 63 to expose the adhesive layer 61. The sensor holder 32 is then secured to the bag in the appropriate location by utilizing the stop member 59 in FIG. 2 as a reference mark to locate the elevation at which it is desired to initiate an alarm. After the sensor holder 32 has been positioned, the sensor head 31 can be slid into position in the holder 32 until it snaps into position between the stop 59 and the detent lug 60. The outlet tube 114 attached to the container 26 can then be positioned in the patient's vessel which is to receive the IV liquid contained within the container 16. After the liquid in the container 16 has been drained from the container to a level causing operation of the liquid level monitoring apparatus as hereinafter described and an alarm initiated, the nurse can remove the sensor head 31 from the sensor holder 32 by sliding it out of the sensor holder away from the stop 59. The container 16 can then be removed from the support member 21 and discarded along with the sensor holder 32 which previously had been secured thereto. A new sensor holder 32 is then taken and secured to the new bag 16 in the manner hereinbefore described and the new bag 16 is hung onto the support member 21. Thereafter, the sensor head 31 can again be slid into the sensor holder 32 in the manner hereinbefore described so that the liquid level can be monitored.

The liquid level sensing apparatus operates on the reflections which occur between the inner surface 91 of the wall 92 of the bag 16 and the interface with the liquid 111 within the bag and which has a liquid level 112. The sensor holder 32 when attached to the bag serves to hold the inner surface 91 of the bag 16 very flat adjacent the sensor head 31 to improve the accuracy of the liquid level monitoring apparatus. This is particularly important where the container 16 is in the form of a flexible plastic bag because the sensor holder prevents deformation of the interface to which the light beam from the sensor head 31 is transmitted and reflected.

It is well known to those skilled in the art, the difference in the indices of refraction of the two different materials, as for example, plastic and air or liquid that the reflection at each interface can be calculated by using the Fresnel equation:

$$\text{Reflectance} = \left( \frac{n_2 - n_1}{n_2 + n_1} \right)^2 \qquad \text{Equation 1}$$

where $n_2$ and $n_1$, are the indices of refraction of the two materials.

When the liquid level sensing apparatus is considered in connection with the present invention, the ray diagrams which would be encountered are shown in FIGS. 9A and 9B. When light beam L1 strikes the plastic container wall 92 above the liquid level 112 reflections occur, one at each of the two surfaces 91 and 93 of the container wall 92 which are identified as points I and II. The magnitude of each reflection is given by the Fresnel equation. Since air is disposed on both sides of the wall 92, the reflected rays $R_{1A}$ and $R_{1B}$ are given by the equations 2 and 3 below wherein the index of refraction of the plastic wall 92 $n_2$ is approximately 1.4 and that of air in $n_1$ is 1.0.

$$R_{1A} = \left(\frac{n_w - n_a}{n_w + n_a}\right)^2 = \left(\frac{1.4 - 1.0}{1.4 + 1.0}\right)^2 = 2.8\% \quad \text{Equation 2}$$

$$R_{1B} = \left(\frac{n_a - n_w}{n_a + n_w}\right)^2 = \left(\frac{1.0 - 1.4}{1.0 + 1.4}\right)^2 = 2.8\% \quad \text{Equation 3}$$

When the light beam L2 strikes the plastic container wall 92 below the liquid level as shown in FIG. 9, then two reflections still occur at points III and IV. However, the magnitude of the reflections are different and can be calculated as follows as shown by equations 3 and 4 below:

$$R_{2A} = \left(\frac{n_w - n_a}{n_w + n_a}\right)^2 = \left(\frac{1.4 - 1.0}{1.4 + 1.0}\right)^2 = 2.8\% \quad \text{Equation 4}$$

$$R_{2B} = \left(\frac{n_f - n_w}{n_f + n_w}\right)^2 = \left(\frac{1.39 - 1.4}{1.39 + 1.4}\right)^2 = 0.001\% \quad \text{Equation 5}$$

The difference in reflection of $R_{1B}$ of 2.8% and that of $R_{2B}$ of 0.001% can be utilized to determine when a liquid is present at the position of being sensed. In the present invention, the apparatus senses only the reflections that change in magnitude since it is impractical and unnecessary to discriminate between the reflections $R_{1A}$ and $R_{2B}$ and $R_{1B}$ and $R_{2B}$ so that the total reflection is measured. The change in reflection between the presence of liquid and the absence of liquid adjacent the plastic wall 92 can then be readily calculated as set forth below in Equation 6.

$$\frac{R}{R_{max}} = \left[\left(\frac{R_{2A} + R_{2B} - R_{1A} + R_{1B}}{R_{1A} + R_{1B}}\right)\right]$$

$$= \left(\frac{(2.87\% + 0.001\%) - (2.8\% + 2.8\%)}{(2.8\% + 2.8\%)}\right)$$

$$R = \frac{2.8\%}{5.6\%} = 50\% \quad \text{Equation 6}$$

This equation shows the changes in reflection can be easily detected provided that stray light from other sources can be ignored or minimized. The detection of stray light is minimized by utilizing three different techniques. The first technique or method is to utilize the lenses 88 and 89 hereinbefore described for the light source and for the detector so that the source of light is focused at the interface between the plastic wall 92 and the liquid with the detector being similarly focused. This reduces the effect of room light by placing a sensor source in focus with the detector.

The effect of stray room light is also reduced by pulsing the source of light to provide a second technique or method. This makes it possible to provide very high intensive light pulses to reduce the effect of stray room light. This has the additional advantage of decreasing power utilization and therefore increasing battery life.

The third technique or method for reducing or minimizing the effect of stray room light is obtained by comparing the signal detected by the first detector in one sensed pair at one location which is compared with the output from a second detector used as a reference in the other sensor pair placed adjacent to the first detector but at a different location. In such a situation, both detectors see the same amount of stray room light but only the first detector sees the additional light from the source. By taking the difference between the two signals, the stray room light signal is subtracted leaving only the source signal. Thus it can be seen that in operation of the sensor, Fresnel reflections are used for sensing the presence of a liquid in the container. The focused source and detector make the sensor relatively immune to stray room light. The use of a second sensor pair as a reference makes the first sensor pair immune to stray room light. The pulsed operation of the sensor source makes the sensor also relatively immune to stray room light.

Utilization of these principles in connection with the circuitry shown in FIG. 8 may now be briefly described as follows. The operational amplifier OA1 with the associated circuitry including the capacitor C1 provides a square wave having a period of approximately two seconds. The capacitor C2 and the operational amplifier 0A2 convert the square wave signal into a short pulse which drives the light emitting diodes 86 in the sensor pairs of the modules 71 and 72 to provide short pulses of light. The detectors 87 which are provided in the sensor pairs in the modules 71 and 72 are connected as common collector photo transistors and generate a voltage which is proportional to the intensity of the light that strikes them. The outputs from the two detectors 87 of the modules 71 and 72 are subtracted from each other by the operational amplifier OA3 and in addition, a fixed reference voltage is generated by the adjustable resistor R15 and the resistor R14 which is subtracted from the voltage from the signal source. Since the gain of the operational amplifier OA3 is large any small difference between the reference voltage and the signal voltage causes a large change in the output of the amplifier OA3.

The output from the operational amplifier OA3 is then utilized to charge capacitor C3 through the diode D2. The voltage on the capacitor C3 rises rapidly when no liquid is present in the container 16 at the level at which the sensing unit is positioned and decays slowly. This serves to lengthen the pulse output and is used to generate a signal to the operational amplifier OA4 which is utilized to provide a signal to operate the buzzer 116 which can be disposed within the case 101 of the monitor unit 12. In addition, the same signal can be supplied to external contacts 117 which can be utilized for powering an external device (not shown) such as an additional remote alarm.

The slow decay of the voltage on the capacitor C3 makes it possible to provide a signal to the operational amplifier OA4 so that it generates a relatively square wave pulse of relatively long duration to actuate the buzzer 116 or an external device connected to the terminals 117. The voltage on the capacitor C3 has a rate of decay which is determined by the resistance connected between the capacitor C3 and ground. This resistance is controlled by the transistor Q1 which forms the low battery indication circuit. When the voltage on battery B1 is greater than approximately 6 volts, the transistor Q1 is turned on and connects the resistor R16 to ground. When the battery voltage of battery B1 drops below approximately 6 volts, the signal formed by the resistor divider R20 and R21 is insufficient to keep the transistor Q1 turned on so it turns off. The resistance of the R16 resistor to ground becomes infinite and the capacitor C3 can never discharge. In fact, the capacitor C3 is discharged to the battery voltage through resistor R19. This causes a continuous buzzing which serves as a low battery indication.

When liquid is present in the container 16 no pulse is generated by the operational amplifier OA3 so that the capacitor C3 remains discharged and the buzzer 116 remains inactivated. However, even if liquid is present in the container, a low battery voltage will still produce a continuous buzzing. Therefore, it is impossible to place into service a liquid level monitoring apparatus which has a low battery voltage without causing a continuous buzzing.

From the foregoing it can be seen that there has been provided a liquid level monitoring apparatus which is particularly suitable for monitoring liquid levels in plastic containers, glass bottles and the like. Since only a single sensor head need be utilized, only one sensor head needs to be positioned by the operator merely by positioning the sensor holder 33, sliding the sensor head 31 into the sensor holder 32. Each use of a container 16 merely requires the disposal of the container 16 itself with a single adhesive backed sensor holder 32. All the remainder of the liquid level sensing apparatus can be saved and reused. Since the sensor holder 32 is relatively simple, it can be formed of a single member of plastic provided with an adhesive backing. Thus it can be very low in cost to minimize the expense in the use of the liquid level monitoring apparatus of the present invention. Also only a single sensor housing is required for each unit. The alignment of the detector and the light emitting diode is fixed in the module eliminating the necessity for adjustment.

The pulse method of sampling and initiating alarms significantly increases the battery life. Even with almost continuous use, the battery should now provide an operating time of approximately one month. A low battery indication is also provided. The liquid level monitoring apparatus can be utilized with colored liquids since transmission of light through the liquid is not required. The liquid level monitoring apparatus is self contained and can be readily moved with the patient without necessity for disconnecting power cords and the like. The sensor holder can be readily modified to accommodate containers which are circular in cross section, as for example, bottles, merely by providing the sensor holder with a curved surface which has a general conformation which corresponds to the curvature of the exterior surface of the bottle.

What is claimed is:

1. In a liquid level monitoring apparatus for monitoring the level of a liquid in a container having a wall with an exterior surface and an interior surface and formed of a material which is substantially transparent to optical energy and which has an index of refraction different from that of the liquid, a sensor holder, adhesive means adapted to secure said sensor holder to the exterior surface of the container at a predetermined level, a sensor head having liquid level sensing means therein, cooperative means carried by the sensor head and the sensor holder for detachably mounting said sensor head on said sensor holder and self-contained power supply means coupled to the sensor head.

2. Apparatus as in claim 1 wherein said sensor head includes a sensor pair comprising a device for providing a source of optical energy and photo-electric means for detecting optical energy, said sensor head being disposed so that said sensor pair lies in a plane which is parallel to the level of liquid in the container, said sensor pair being directed so that optical energy is directed into one region and is detected in the same region.

3. Apparatus as in claim 2 together with lens means for focusing the optical energy onto said area and additional lens means for detecting optical energy in said area.

4. Apparatus as in claim 2 together with means for causing said optical energy to be supplied in pulses.

5. Apparatus as in claim 2 wherein said sensor head includes an additional sensor pair and wherein said sensor pair is positioned below said first named sensor pair so that the second sensor pair can be utilized for providing a reference to minimize the effect of ambient stray light.

6. Apparatus as in claim 2 wherein said optical energy is infrared.

7. Apparatus as in claim 1 wherein said sensor head is slidably mounted in said sensor holder.

8. Apparatus as in claim 7 wherein said cooperative means includes means for ensuring that the sensor head can only be positioned in said sensor holder in a predetermined orientation.

9. Apparatus as in claim 1 together with means connected to the first sensor pair for initiating an alarm when the liquid level falls below a predetermined level.

10. In a sensor holder for use in a liquid level monitoring apparatus for monitoring the level of liquid in a container at least a portion of which is substantially transparent for use with a detachable sensor head having liquid level sensing means therein, the sensor holder including a plate-like member having an exterior surface, a pressure sensitive adhesive carried by said exterior surface, said adhesive having an adhesive surface, removable protective means protecting said adhesive surface and cooperative mating means carried by the sensor holder for detachably engaging the sensor head and for retaining the same in engagement therewith.

11. A sensor holder as in claim 10 wherein said member is provided with an opening therein and wherein said opening is in registration with the sensor head when the sensor head is detachably mounted thereon.

12. Apparatus for use in liquid level monitoring, a container having a wall formed of a substantially transparent material, a sensor holder having a surface and having an adhesive material formed thereon, the sensor holder being mounted on the exterior surface of the wall of the container with an adhesive engagement with the exterior surface of the bag, said sensor holder having cooperative mating means mounted thereon and a sensor head having liquid level sensing means therein detachably mounted in said sensor holder.

13. Apparatus as in claim 12 wherein said sensor holder includes an opening provided therein and wherein said sensor head has a sensor pair, mounted therein and adapted to operate through the opening in the sensor holder.

14. Apparatus as in claim 13 wherein said sensor head has an additional sensor pair mounted therein.

15. Apparatus as in claim 14 wherein said first named and additional sensor pairs lie in parallel planes parallel to the surface of the liquid in the container.

16. Apparatus as in claim 15 together with circuitry interconnecting said first named and additional sensor pairs so that one of the pairs serves as a reference pair to minimize the effects of stray optical energy.

17. In a method for detecting the level of a liquid in a container having a wall formed of a material which is substantially transparent to optical energy and having an exterior surface and an interior surface and an index of refraction different from the index of refraction of the liquid in the container, directing optical energy through the wall of the container so that energy is reflected from the exterior and interior walls of the container, detecting the reflections from the exterior and interior surfaces of the wall of the container at one location and detecting when a change occurs in the reflections from the exterior and interior walls of the container to thereby ascertain when the liquid level in the container falls below a predetermined level in the container.

18. A method as in claim 17 together with the step of pulsing the optical energy to minimize the effect of stray optical energy.

19. A method as in claim 17 together with the step of detecting optical energy at an additional location spaced below said one location to provide a reference to substantially eliminate the effects of stray optical energy.

* * * * *